(12) United States Patent
Gadgil

(10) Patent No.: US 9,677,046 B2
(45) Date of Patent: Jun. 13, 2017

(54) SYSTEM FOR IN-SITU MANAGEMENT OF PH OF CULTURE

(71) Applicant: Council of Scientific & Industrial Research, New Delhi (IN)

(72) Inventor: Mugdha Chetan Gadgil, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/418,880

(22) PCT Filed: Jul. 31, 2013

(86) PCT No.: PCT/IN2013/000475
§ 371 (c)(1),
(2) Date: Jan. 30, 2015

(87) PCT Pub. No.: WO2014/020617
PCT Pub. Date: Feb. 6, 2014

(65) Prior Publication Data
US 2015/0210980 A1 Jul. 30, 2015

(30) Foreign Application Priority Data
Jul. 31, 2012 (IN) .......................... 2302/DEL/2012

(51) Int. Cl.
*A61K 33/06* (2006.01)
*C12N 5/00* (2006.01)
*C12N 1/20* (2006.01)

(52) U.S. Cl.
CPC ............. *C12N 5/0068* (2013.01); *C12N 1/20* (2013.01); *C12N 2500/16* (2013.01); *C12N 2500/34* (2013.01); *C12N 2500/60* (2013.01); *C12N 2533/30* (2013.01); *C12N 2539/00* (2013.01)

(58) Field of Classification Search
CPC . A61K 33/06; C12N 2500/14; C12N 2500/16
See application file for complete search history.

(56) References Cited

U.S. PATENT DOCUMENTS

| 4,699,793 A | * | 10/1987 | Eguchi | .................... A23L 27/25 426/41 |
| 6,180,688 B1 | * | 1/2001 | Rheinberger | .......... A61K 6/083 523/116 |
| 2013/0337566 A1 | * | 12/2013 | Schmidt | ............... C12N 5/0068 435/404 |

FOREIGN PATENT DOCUMENTS

| WO | WO 2004/000918 A1 | 12/2003 |
| WO | WO 2007/112436 A2 | 10/2007 |
| WO | WO 2012/092542 | * 7/2012 |

OTHER PUBLICATIONS

Gupta, P. et al. 2002 "Hydrogels: from controlled release to pH-responsive drug delivery" *DDT* 7: 569-579.
Pradhan, K. et al. 2012 "In situ pH maintenance for mammalian cell cultures in shake flasks and tissue culture flasks" *American Institute of Chemical Engineers Biotechnol Prog* 28: 1605-1610.
Scheidle, M. et al. 2011 "Controlling pH in shake flasks using polymer-based controlled-release discs with pre-determined release kinetics" *BMC Biotechnology* 11: 25 (in 11 pages).
Schmaljohann, D. 2006 "Thermo- and pH-responsive polymers in drug delivery" *Advanced Drug Delivery Reviews* 58: 1655-1670.
Zhou, H. et al. 2009 "pH measuremenet and a rational and practical pH control strategy for high throughput cell culture system" *American Institute of Chemical Engineers Biotechnol Prog* 26: 872-880.

* cited by examiner

*Primary Examiner* — Ruth Davis
(74) *Attorney, Agent, or Firm* — Knobbe, Martens, Olson & Bear, LLP

(57) ABSTRACT

Disclosed is a hydrogel composition loaded with a base that regulates and maintains the pH of cell culture media. The invention particularly discloses in situ pH managing hydrogels (pHmH) loaded with base $Mg(OH)_2$ for pH control in small scale cultures comprising adherent mammalian cells, suspended mammalian cells, microorganisms, a microorganism with plasmids and the like thereof.

14 Claims, 9 Drawing Sheets

(a)

(a)

(b)

(c)

(a)

(b)

(c)

(a)

(b)

(c)

(a)

(b)

(c)

(d)

SYSTEM FOR IN-SITU MANAGEMENT OF PH OF CULTURE

TECHNICAL FIELD OF INVENTION

The present invention relates to a system for in-situ management of pH of culture comprising a carrier and a base. Particularly, the present invention relates to a hydrogel loaded with base that manages and maintains pH in a cell culture media without any additional infrastructure for pH measurement. More particularly, the invention particularly discloses in situ pH managing hydrogels (pHmH) loaded with base for pH control in small scale cell culture formats comprising adherent mammalian cells, suspended mammalian cells, microorganisms, a microorganism with plasmids, insect cells and like thereof. The invention also discloses a method for pH management and maintenance using the hydrogel loaded with base of the invention.

BACKGROUND AND PRIOR ART

Extracellular pH has been shown to affect cell physiology, though its effect is not as widely studied as other physical parameters like temperature. Unless controlled, pH of a cell culture process can vary during the course of culture, and usually decreases due to formation of waste metabolites like organic acids.

Several references point out that commercial cell culture processes such as for recombinant protein production are affected by pH. pH is typically controlled in bioreactors cultivating animal cell cultures between 6.8 to 7.15 via measurement and subsequent base/$CO_2$ addition, and has been automated in commercially available scale down micro bioreactors (e.g Simcell, Seahorse Bioscience, MA, USA). However, pH is not controlled in widely used small scale culture platforms like shake flasks for suspension cultures due to lack of simple methods, though robotic instrumentation is available commercially for the same (e.g. DASGIP (Germany) and TAP (UK)).

Lack of pH control can result in sub optimal screening due to differences in performance under controlled and uncontrolled pH conditions. Bareither and Pollard (Biotechnol. Prog. 2011; 27:2-14) have recently reviewed small-scale parallel culture formats for accelerated process development and noted that: "The simplified systems of shake flasks and microtiter plates provide significant high throughput capability. Yet they carry less instrumentation which limits the opportunity for data quality and quantity. For this reason they remain as screening tools without implementation of robust pH and DO (dissolved oxygen) control". To circumvent this, scale down microbioreactors have been recently commercially introduced which are able to control pH of mammalian cell cultures via measurement and subsequent base/CO2 addition (e.g. Ambr™, TAP Biosystems, UK which was demonstrated to maintain pH within ±0.2 units from the set point 7). However, the said pH control involves investment in additional infrastructure.

Zhou et al (*Biotechnol. Prog.* 2010; 26: 872-880) have reported using SNARF-4F 5-(-and 6)-carboxylic acid pH monitoring for multiwell plates and shake flasks, followed by calculations of required base addition based on a mathematical model, which also needs instrumentation for continuous control.

Further pH is an important parameter that can affect microbial cell growth. pH can decrease significantly during culture in the presence of carbon sources like glucose due to overflow metabolism and a change in pH beyond the permissive range of the organism affects cell growth. It is estimated that more than 90% of all cultures in biotechnology are carried out in shake flasks which traditionally have no control over pH. Decrease in pH of the culture can thus contribute to limited cell densities achieved in shake flasks. To prevent excessive pH drifts, culture medium can be supplemented with high buffer concentrations. However, high buffer concentrations result in increased osmolarity of the culture medium and may be inhibitory to the growth of the micro-organism. Moreover when the amount of protons produced exceeds the capacity of the buffer, the buffer will no longer be able to prevent changes in pH.

Scheidle et al. (*BMC Biotechnol.* 2011; 11: 25) have recently demonstrated a system releasing sodium carbonate for pH control in a microbial culture for 14 hours, wherein polymer-based controlled-release discs embedding sodium carbonate crystals are used for controlling the pH in shake flasks enabled the successful cultivation of *E. coli* K12 and *E. coli* BL21 pRSET eYFP-IL6 in mineral media with glycerol and glucose as carbon sources, respectively.

US2009190135 (Clarizia Lisa et al.) discloses method for maintaining an optimal cell culture pH, comprising providing a pH-sensitive hydrogel comprising a pH-regulating agent or buffer to the cell culture that comprises mouse embryonic stein cells under conditions, such that the regulating agent or buffer is released into the cell culture in response to a change in the pH of the cell culture, such that the optimal cell culture pH is maintained. Also it discloses the autoregulatory nature of the hydrogels' activity which leads to the periodic release of base, maintaining the pH within or very close to the optimal pH range for the cell culture for up to 4 days, refer FIG. 9. However there is no teaching about microbial pH control.

Chen A, *Biotechnol. Bioeng.* 2009; 102: 148-160, reported Twenty-four well plate miniature bioreactor system as a scale-down model for cell culture process development but suffer from economic disadvantages.

In view of the prior art pH control via measurement and base addition is not easily possible in small-scale culture formats like tissue-culture flasks and shake flasks.

Hydrogels are hydrophilic polymers that absorb water- and are insoluble in water under physiologic conditions due to the existence of a three-dimensional network. Also the application of hydrogels has been widely reported for controlled drug release and tissue engineering.

Therefore the inventors have developed a hydrogel based system loaded with a base for in situ pH maintenance.

The non-maintenance of pH in the desired narrow range also prevents shake flasks to precisely and accurately mimic bioreactor based operation for initial screening during cell line and process development for recombinant protein production in mammalian cells and other such similar operations.

These hydrogels can also be suitably modified with reduced cross-linking and increased surface area for application to faster growing microbial cultures.

OBJECTS OF INVENTION

The main object of the invention is to provide a system for in-situ management of pH of culture comprising a carrier and a base.

Another object of the present invention is to provide in-situ pH management system that maintains pH, without the need to measure the pH on a periodic basis.

Another object of the present invention is to provide pH managing hydrogel (pHmH) loaded with base for in-situ pH maintenance for small scale culture formats without the need for any additional infrastructure.

Yet another objective of the invention is to provide an in situ pH maintenance system that allows increase in biomass and/or product yield when compared with a control.

SUMMARY OF INVENTION

Accordingly, the present invention provides a system for in-situ management of pH of culture comprising a carrier and a base wherein said base is selected from $Mg(OH)_2$ or $Ca(OH)_2$, said carrier is selected from hydrogel, polymer matrices selected from silicone elastomer, encapsulation for base, membranes, coating films, said carrier is non-responsive to pH change of culture.

In an embodiment of the present invention the carrier used is a hydrogel.

In one embodiment of the present invention the hydrogel comprises 2-hydroxyethyl methacrylate (HEMA) as monomer; Azoisobutyronitrile, (AIBN) as initiator and optionally ethylene glycol dimethacrylate (EGDMA) as cross linker.

In another embodiment of the present invention said culture comprises medium and cells selected from unmodified or genetically modified animal cells, microbial cells, insect cells, stem cells and mesenchymal stem cells.

In another embodiment of the present invention said culture is grown in a medium comprising glucose, and optionally a buffer.

Still in another embodiment of the present invention the pH of the culture is managed between 5-9.

Still in another embodiment of the present invention the pH of the culture is managed for a period of up to 15 days.

Still in another embodiment of the present invention the release of $Mg(OH)_2$ or $Ca(OH)_2$ is dependent on pH of culture.

Still in another embodiment of the present invention said pH dependence of release of base is independent of carrier composition.

Still in another embodiment of the present invention the in-situ management does not require periodic measurement of pH.

ABBREVIATIONS pHmH: pH managing hydrogel
HEPES: 4-(2-hydroxyethyl)-1-piperazineethanesulfonic acid
HEMA: 2-hydroxyethyl methacrylate
EGDMA: Ethylene glycol dimethacrylate
AIBN: Azoisobutyronitrile
DMEM: F12 medium: Dulbecco's Modified Eagle's Medium/Nutrient Mixture F-12
FBS: Fetal bovine serum
CD: Chemically Defined
CHO: Chinese Hamster Ovary
A549 cells: human lung carcinoma
MOPS buffer: 3-(N-morpholino) propanesulfonic acid buffer

DETAILED DESCRIPTION OF INVENTION

The invention will now be described in detail in connection with certain preferred and optional embodiments, so that various aspects thereof may be more fully understood and appreciated.

In accordance with the objectives of the invention, the inventors provide a system comprising a carrier and a base for in-situ management of pH.

In a preferred embodiment, the invention provides a hydrogel as carrier, wherein the carrier is loaded with base which manages/maintains pH of cell culture media without the need of any additional infrastructure.

The additional infrastructure includes monitoring pH or measuring pH through, mathematical model, robotic instruments, Optical Transmittance, dye indicator and like thereof.

In preferred embodiment, the invention provides base loaded hydrogel composition for in-situ regulation and maintenance of the pH in small scale culture formats without pH measurements, comprising a monomer, an initiator, a base and optionally a cross linker. According to the embodiment above the monomer is 2-hydroxyethyl methacrylate (HEMA); the cross-linker is ethylene glycoldimethacrylate, (EGDMA); the initiator is Azoisobutyronitrile, (AIBN) and the base is $Mg(OH)_2$.

In a preferred embodiment, the base is $Mg(OH)_2$.

The inventors have selected magnesium hydroxide as a base for pH maintenance due to its low solubility product ($Ksp=1.8\times10^{-11}$), that might reduce 'leakage' of base which is important for long term culture, and for its effect on osmolarity, since the release of two $OH^-$ is accompanied by only one $Mg^{+2}$. Also, as for any other base, the solubility of magnesium hydroxide increases with a decrease in pH, which is expected to result in an increase in hydroxyl ion release rate with decreasing pH.

Further in the instant hydrogel composition, the base is dispersed in the hydrogel, or the base is within the hydrogel as a reservoir. Further the base is included as a layer between two layers of the hydrogel. It may be further evident that the release of the base from the carrier is dependent on the pH of the culture.

In an embodiment, the culture is grown in a medium comprising glucose.

Figure 5:
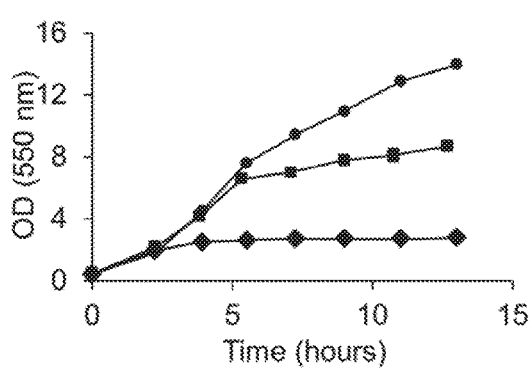
FIG. 5 depicts (a) Growth of E. coli K12 in LB-glucose with and without pHmH-2 (b) Glucose consumption of E. coli K12 in LB-glucose with and without pHmH-2 (c) pH profiles of E. coli K12 cultures in LB-glucose with and without pHmH-2. Control, without pHmH-2 ♦, With single pHmH-2 ■ and with staggered addition of two pHmH-2 ●.
Figure 5:
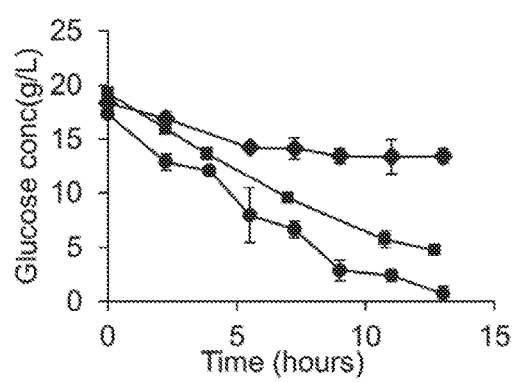
Figure 5:
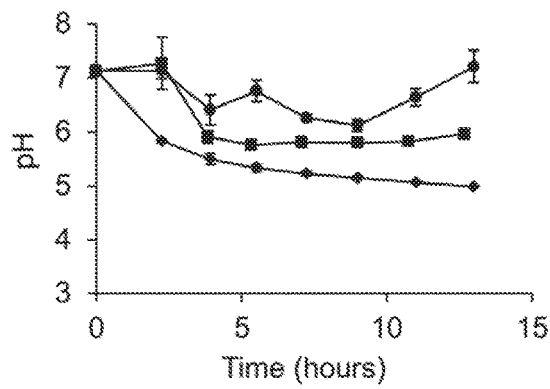
Figure 6:
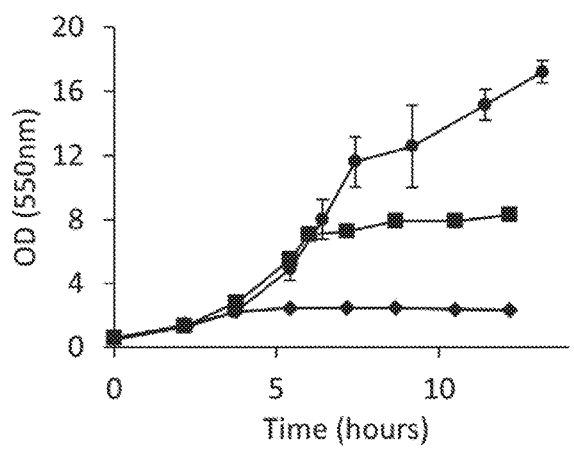
FIG. 6 depicts (a) Growth of E. coli K12 in Modified Wilms and Reuss medium (no buffer) with and without pHmH-2 (b) Glucose consumption of E. coli K12 in Modified Wilms and Reuss medium (no buffer) with and without pHmH-2 (c) pH profiles of E. coli K12 cultures in Modified Wilms and Reuss medium (no buffer) with and without pHmH-2. Control, without pHmH-2 ♦, With single pHmH-2 ■ and with staggered addition of two pHmH-2 ●.
Figure 6:
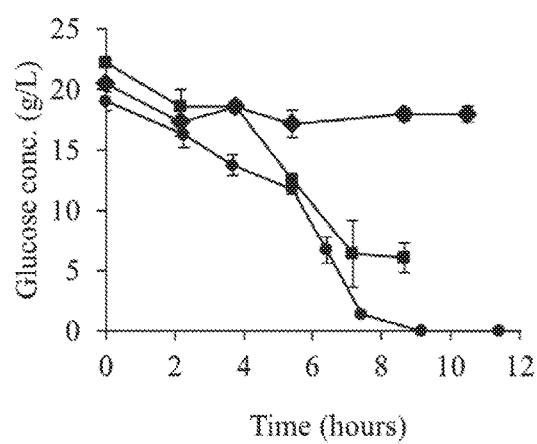
Figure 6:
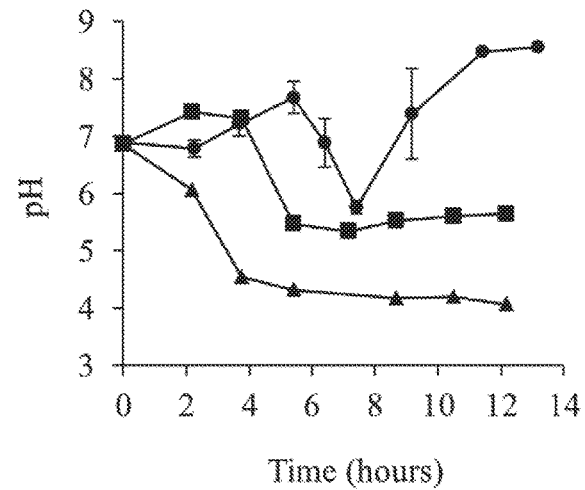

In an optional embodiment, the culture is grown in a medium comprising buffer. With reference to FIGS. 5, 6, demonstrating cultures with no buffer and FIGS. 7 and 8 demonstrating cultures with buffer, the improved growth of respective cells is demonstrated with pHmH-2.

In another preferred embodiment, the invention provides method for preparation of base loaded hydrogels comprising steps of;
a) mixing of monomer 2-hydroxyethyl methacrylate (HEMA) and optionally a cross-linker, ethylene glycol dimethacrylate, EGDMA, in suitable molar ratio;
b) dissolving an initiator Azoisobutyronitrile, (AIBN) to solution in step a);
c) sterilizing the obtained solution from step b) by filtering through a 0.22 μm filter;
d) adding sterilized base i.e. $Mg(OH)_2$ to solution in step c); and
e) allowing to polymerize the mixture in step d) in a at temperature in the range of (60° to 90°) for 2-3 hrs under aseptic condition to obtain pH managing hydrogel (pHmH) disc. In an embodiment, the pHmH may be prepared and then sterilized by means well known in the art such as autoclaving, gamma irradiation and such like.

According to the invention, the monomer 2-hydroxyethyl methacrylate (HEMA) and a cross-linker, ethylene glycol dimethacrylate, (EGDMA) are mixed, wherein the molar ratio of (HEMA:EGDMA) is present in the range of 80:20 to 100:0; preferably 85:15 to 93:7 mol/mol of (HEMA: EGDMA) in the presence of an initiator i.e. Azoisobutyronitrile, (AIBN) in the concentration ranging from 0.1% to 0.8%; preferably 0.5%. Further the solution containing HEMA, EGDMA with dissolved AIBN is sterilized by filtering through a 0.22 nm filter, subsequently the sterilized $Mg(OH)_2$, is added to the above solution and the mixture is allowed to polymerize in a glass disc at temperature in the range of 60° to 90° C. for 2-3 hours under aseptic conditions to obtain pH managing hydrogels (pHmH) discs, which are washed in water for 2-4 days to remove unreacted/unpolymerized monomer.

In another embodiment, the instant pHmH discs are prepared preferably in molar ratio of 93:7 mol/mol of HEMA:EGDMA.

In yet another embodiment, the invention provides in-situ pH managing hydrogel (pHmH) loaded with $Mg(OH)_2$ that maintains pH of cell culture at least between ±0.3 units of desired pH, without the need for measurement of pH. The prepared hydrogel in the form of disc used for in situ pH maintenance for cell culture in small scale formats, wherein the cell culture is selected from the group consisting of mammalian cells in suspension, insect cells, adherent mammalian cells, microbial cells, microbial cells expressing plasmids.

The small-scale culture formats are not limited to tissue-culture flasks, shake flasks or spinner flasks.

The mammalian cell in suspension is selected from the group of unmodified or genetically modified Chinese Hamster Ovary (CHO) cell line, human bone marrow-derived mesenchymal stem cells, (hBMMSCs), mouse hybridoma cell line, mouse myeloma cell line, Baby Hamster Kidney (BHK) cell line, human embryonic kidney (HEK) cells, HEK 293, PER.C6 and human retinal cells, The adherent mammalian cell is selected from the group of unmodified or genetically modified A549 cells, CHO, BHK, HEK 293, PER.C6, mouse myeloma cells, stem cells and primary cells derived from human tissue.

The microbial cell is selected from the group consisting of unmodified or genetically modified *Pseudomonas, Salmonella, Geobacter, Bacillus, Pichia, Saccharomyces, Hansenuia* and *Escherichia coli* cells.

In an another embodiment, the mammalian cells in suspension is particularly 'culture of a suspension Chinese Hamster Ovary (CHO) cell line in CD CHO medium', whereas the adherent mammalian cells are 'A549 cells in DMEM:F12 containing 10% FBS', the microbial cell is '*E. coli* K12 cells' and the microbial cells expressing plasmids are '*E. coli* TOP10 cultures transformed with plasmid DNA'.

In yet another embodiment, the pHmH of the invention maintains the pH of medium within ±0.3 units of the set point. The pH of suspension cells is maintained at ±0.2 units of desired pH; wherein the desired pH is in the range of 7 to 7.5.

Accordingly (pHmH) hydrogel maintain the pH in between 6.8 and 7.2 for suspension Chinese Hamster Ovary (CHO) cell line in CD CHO medium.

Further the instant pH managing hydrogels (pHmH) loaded with magnesium hydroxide were evaluated in a fed batch culture of a suspension Chinese Hamster Ovary (CHO) cell line to assess the culture pH profile as compared to control cultures, where pH was allowed to drift, as is typical in shake flasks. pHmH disc addition allowed pH to be maintained between 6.8 to 7.2 for suspension CHO cells in CD CHO medium, the in situ pH control using the pHmH described herein, can increase the utility of shake flasks as a screening tool for animal cell based bioprocesses without the need for any additional infra structure.

In yet another embodiment, the pHmH of the invention maintains the pH of adherent cells at ±0.1 units of desired pH; wherein the desired pH is in the range of 7 to 7.5.

The instant hydrogel maintain the pH between 7.3 and 7.5 for adherent A549 cells in DMEM:F12 containing 10% FBS in tissue culture flasks.

In another embodiment of the invention, the pHmH is used to increase biomass yields for microbial culture as exemplified in herein below. As embodied herein and with reference to the examples provided, the pHmH manages and maintains the pH of the medium without the need for periodic requirement of measurement of the pH of the medium. The pH is maintained within the desirable range for a period of up to 15 days.

In an another embodiment, the base loaded hydrogel maintains the pH of microbial cell culture comprising of bacterial cells particularly *Escherichia coli*.

Accordingly the invention provides magnesium hydroxide loaded hydrogels for pH management to maintain pH in permissive range for optimal growth of *E. coli* K12 cell cultures. *E. coli* cells produce acetic acid under conditions of excess glucose due to overflow metabolism resulting in a decrease in culture pH. In the instant invention, the inventors demonstrate the use of magnesium hydroxide loaded hydrogels to increase the biomass yield for *E. coli* K12 and volumetric plasmid yield in an *E. coli* TOP10 strain transformed with a plasmid.

2 Hydroxy ethyl methacrylate (HEMA) (97% pure), Ethylene glycol dimethylacrylate (EGDMA) and Dichlorodimethylsilane were purchased from Sigma Aldrich (MO, USA) and Azoisobutyronitrile, the thermal initiator was purchased from Spectrochem (India). *E. coli* K12 and a clone of TOP10 *E. coli* (Invitrogen Corporation, CA, USA) transformed with a 5 kb plasmid cells were used. GOD/POD glucose assay kit was purchased from Beacon diagnostics, India. QIAprep Spin Miniprep Kit from QIAGEN (Hilden, Germany) was used for plasmid DNA purification.

Media Composition and Culture Conditions:

LB broth consists of 10 g/L tryptone, 5 g/L yeast extract and 10 g/L NaCl. 20 g/L glucose was added to LB broth after autoclaving to serve as carbon source. For the culture of TOP10 *E. coli* cells, culture medium was supplemented with 100 μg/ml ampicillin.

The modified Wilkins and Reuss medium was prepared as described by (Scheidle et (al., 2011) and consists of 20 g/L glucose; 5 g/L $(NH_4)_2SO_4$; 0.5 g/L $NH_4Cl$; 3 g/L $K_2HPO_4$; 2 g/L $Na_2SO_4$; 0.5 g/L $MgSO_4.7H_2O$; 0.01 g/L thiamine hydrochloride; 1 mL/L trace element solution (0.54 g/L $ZnSO_4.7H_2O$; 0.48 g/L $CuSO_4.5H_2O$; 0.3 g/L $MnSO_4.H_2O$; 0.54 g/L $CoCl_2.6H_2O$; 41.76 g/L $FeCl_3.6H_2O$; 1.98 g/L $CaCl_2.2H_2O$; 33.39 g/L $Na_2EDTA$ (Titriplex III). 3-(N-morpholino)propanesulfonic acid (MOPS) was added at indicated concentrations in some experiments.

Analytical Methods:

Growth was monitored by measuring the optical density (550 nm) at regular intervals after appropriate dilution. pH of the culture supernatant was measured using a pH electrode (Sentek, UK). Samples were stored at −20° C. and glucose concentration was measured using GOD/POD glucose assay kit (Beacon Diagnostics, India). All experiments were performed in triplicates.

Swelling Kinetics:

The empty pHmH was dried in an oven at 50° C. for a day to complete dryness to study the swelling kinetics. The weight of pHmH was measured before and after immersing in water to determine the extent of swelling. The swollen weight was measured at several instances after removing the surface water with blotting paper. Swelling ratio was calculated using the formula:

$$\text{Swelling ratio} = (W_s - W_d)/W_d,$$

where $W_d$ is the weight of the dry pHmH and $W_s$ is the weight of the swollen pHmH.

A pHmH xerogel was added to water, and the increase in weight of the pHmH was measured as a function of time to estimate swelling kinetics. Empty pHmH reached equilibrium swelling in approximately 4 hours. The pHmH reached an equilibrium swelling ratio of 67%.

The present invention is illustrated herein below with examples, which are illustrative only and should not be construed to limit the scope of the present invention in any manner.

EXAMPLES

Example 1

Preparation of Hydrogel (pHmH-1)

Poly-HEMA hydrogels were synthesized using monomer, 2-hydroxyethyl methacrylate [HEMA, 97% pure] and a cross-linker, ethylene glycol dimethacrylate, EGDMA (Sigma-Aldrich Corp, USA) at 93:7 mol/mol HEMA: EGDMA in the presence of an initiator Azoisobutyronitrile, AIBN (0.5%, Sigma Aldrich Corp, USA). The solution containing HEMA, EGDMA with dissolved AIBN was sterilized by filtering through a 0.22 μm filter. 100 mg sterile $Mg(OH)_2$, sterilized by autoclaving at 15 psi and 121° C. for 20 minutes, was added to 500 μl of the above solution and the mixture allowed to polymerize in a 1.3 cm diameter glass disc at 75° C. for 3 hours followed by 90° C. for 15 minutes under aseptic conditions. These discs, referred to hereafter as pH managing hydrogels-1 (pHmH-1), were washed in water for three days Example 2

Preparation of Hydrogel (pHmH-2)

0.5% w/v Azobisisobutyronitrile (AIBN) was dissolved in 1.5 ml 97% pure 2-Hydroxyethyl methacrylate. After dissolution, the mixture was poured onto a glass surface. 150 mg of a $Mg(OH)_2$ was added to the solution and mixed. The gel mixture was allowed to polymerize at 75° C. for 3 hours. The hydrogels prepared had a surface area of ~23 cm². The hydrogels were washed in water for one day to remove any unreacted monomer. These discs are referred to hereafter as pH managing hydrogels-2 (pHmH-2)

Example 3

Preparation of Hydrogel (pHmH-3)

0.5% w/v Azobisisobutyronitrile (AIBN) was dissolved in 1.5 ml 97% pure 2-Hydroxyethyl methacrylate. After dissolution, the mixture was poured onto a glass surface. 100 mg of a $Mg(OH)_2$ was added to the solution and mixed. The gel mixture was allowed to polymerize at 75° C. for 3 hours. The hydrogels prepared had a surface area of ~23 cm². The hydrogels were washed in water for one day to remove any unreacted monomer. These discs are referred to hereafter as pH managing hydrogels-3 (pHmH-3)

Example 4

Rate of Release of Mg+2 from pHmH at Different pH

Figures 1A, 1B:
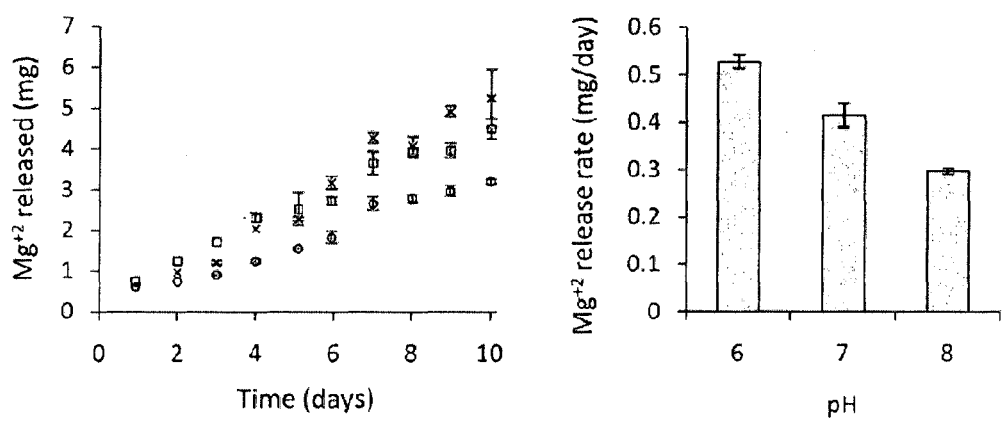
FIG. 1 depicts Effect of pH on release of $Mg^{+2}$ from pHmH discs. (a) One pHmH-1 was added to 100 mL of 200 IBM HEPES solution at pH 6 (cross), 7 (square), or 8 (circle), respectively. Samples were taken every day to measure Magnesium concentration. N=3. Error bars indicate one standard deviation above and below the average. (b) Release rate of $Mg^{+2}$ from pHmH-1 at pH 6, 7, and 8.
FIG. 1c depicts pHmH-3 of a different composition in comparison to pHmH-1 showing release rate can be changed by changing parameters like cross linking density, geometry of the hydrogel.
Figure 1C:
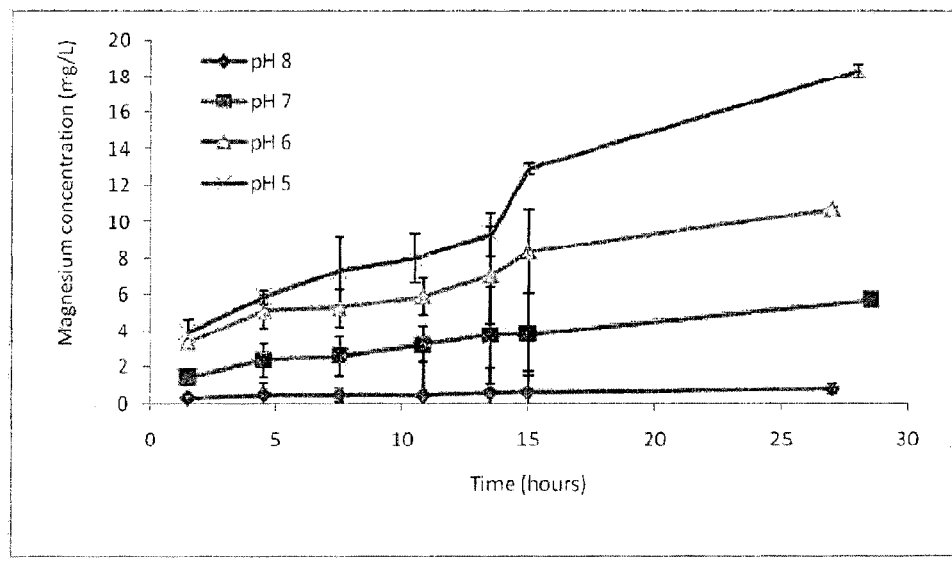
Figure 2:
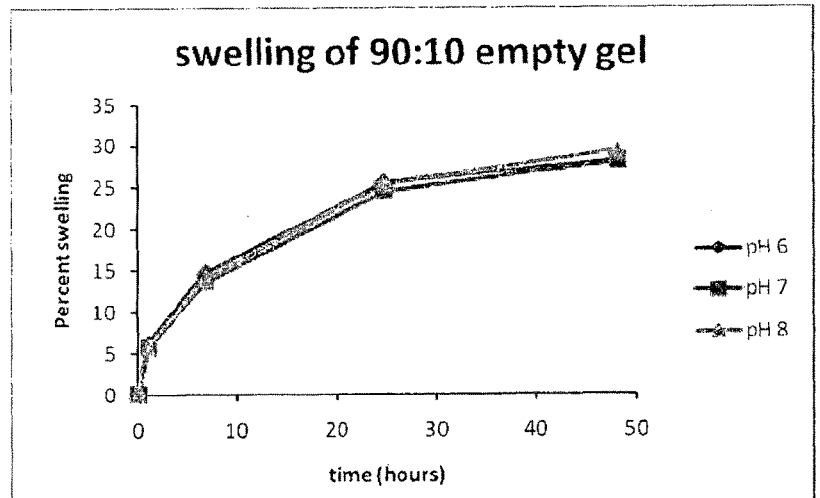
FIG. 2 depicts percent swelling of pHmH-1 at different pH.

The release of Magnesium from the pHmH-1 of the invention over different pH and the management of the pH and its maintenance in culture medium is evaluated, wherein the release rates of $OH^-$ can be changed by changing parameters like cross linking density, geometry of the hydrogel and the identity of the base, with reference to FIG. 1, it is observed that release of $Mg^{+2}$ from pHmH discs is dependent on pH even though the hydrogel is not pH sensitive (Refer FIG. 2).

One pHmH-1 was added to 100 mL of 200 mM HEPES solution at pH 6, 7 or 8 respectively, and incubated under shaking conditions at 37° C. Experiment at each pH was performed in triplicates. Samples were taken once every day for the measurement of $Mg^{+2}$ concentrations as described below. The pH of the solution was measured everyday to ensure no change. For the experiment at pH 6, pH was adjusted on days 8 by addition of $H_2SO_4$.

Mg+2 Release from pHmH at pH 6, 7 and 8

FIG. 1 shows the cumulative $Mg^{+2}$ released from the pHmH-1 at different pH values. The release rate of [$OH^-$] is calculated from this data based on stoichiometry. The total amount of $Mg^{+2}$ released over typical culture duration is thus a small fraction of the initial loading of magnesium hydroxide in the pHmH-1. The slope of the graph of Mg+2 released vs. time in FIG. 1a provide estimates of the release rate of Mg+2 at the different pH. The release rate can be seen increasing with decreasing pH (FIG. 1b). Since HEMA: EGDMA hydrogels are not known to be pH responsive, this pH responsive behavior of the release rate is probably observed due to the phenomenon of increasing solubility of a base with decreasing pH.

pHmH-3 hydrogels were added to phosphate buffers at different pH to evaluate release of magnesium at different pH values.

Phosphate buffer comprised $NaH_2PO_4$ and $Na_2HPO_4$ in the following amounts, dissolved in 500 ml water: for pH 8-1.4 g and 24.97 g respectively, pH 7-7.836 g and 15.466 g respectively, pH 6-12.143 g and 3.217 g respectively pH 5-13.614 g and 0.45 g Gels were pre-swollen in water and added to the 500 ml phosphate buffers at the different pH, and maintained at 37° C. with shaking at 200 rpm. All experiments were run in triplicate. Samples were withdrawn at regular intervals. Mg concentration was measured using SPECTRO ARCOS SOP Inductively Coupled Plasma spectrometer (SPECTRO Analytical Instruments, Germany). With reference to FIG. 1c, the release rate of $Mg^{+2}$ increases with decrease in pH.

The FIG. 1a and is clearly shows that the release rate of the base may be tailored by varying the composition of the carrier.

Example 5

Evaluation of pH Maintenance on Suspension CHO Cell Culture

Figure 3:
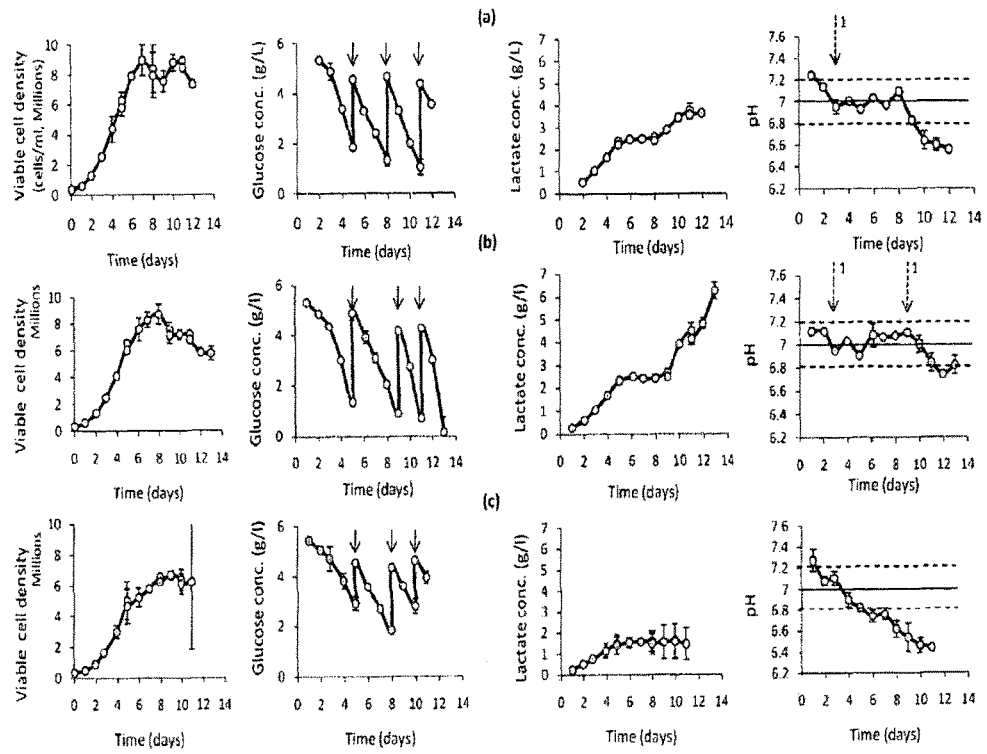
FIG. 3 depicts effect of pHmH-1 disc addition on pH profile during culture of suspension CHO cells. CHO cells were seeded in shake flasks in 20 mL CD CHO medium containing 8 mM glutamine without antibiotics at $0.3\times10^6$ cells/mL and fed with glucose and protein hydrolysate at times indicated by solid arrows. Four grams per liter hydrolysate was added at the first feed, and 2 g/L at subsequent feed additions. pHmH-1 disc was added to the culture at time(s) indicated by dotted arrows. Number of pHmH-1 discs added is indicated next to the dotted mow. Cultures were run in duplicates. (a) Addition of single pHmH-1 disc. (b) Staggered addition of two pHmH-1 discs. (c) Control (without pHmH-1 disc). Error bars indicate one standard deviation above and below the average.

A suspension CHO cell line (Inbiopro) was used to evaluate the ability of the pHmH-1 discs as exemplified in example 1 to maintain pH in suspension cells during a fed batch culture. Cells were inoculated at a density of $0.3 \times 10^6$ cells/ml in 20 ml CD CHO medium (Invitrogen. Corporation, CA, USA) containing 8 mM glutamine, without antibiotics in shake flasks (37° C., 10% CO2, 110 rpm) and fed with glucose and protein hydrolysate at indicated times. 4 g/l hydrolysate was added at the first feed, and 2 g/l at subsequent feed additions. Glucose concentrations are shown in FIG. 3. Hydrogels were added on two schedules (a) Single pHmH-1 added on day 3 (b) Staggered addition: The first pHmH-1 disc was added on day 3, the second pHmH-1 disc was added at the time of the second feed. Samples were taken every day for measuring cell density, viability, glucose and lactate concentrations (the cells make lactate which affects pH) and pH. Cell density was quantified using a haemocytometer. Viability was assessed using a tryptan blue dye exclusion assay. Glucose and lactate concentrations were measured on a YSI Biochemistry analyzer. 100-150 µl of the cell supernatant after centrifugation of the sample was allowed to reequilibrate with 10% $CO_2$ in the incubator. pH was immediately measured using a pH probe (Sentek, UK).Control cultures showed decrease in pH to ~6.4 towards the end of culture. Staggered addition of two pHmH discs enabled pH to be largely maintained between 6.8 to 7.2 while culture viability was greater than 85% (FIG. 3).

Example 6

Evaluation of pH Maintenance on Adherent Cells pHmH-1 discs were also evaluated for pH maintenance for adherent cells using A549 as a model system.

A549 cells were seeded in 8 ml DMEM:F12 medium with 2 g/l sodium bicarbonate and 10% FBS without antibiotics in 25 $cm^2$ tissue culture flasks with two pHmH-1 discs. Control cultures were likewise seeded in triplicate without the addition of pHmH-1 disc. All flasks were incubated at 37° C. under 5% $CO_2$. 150 µl samples were withdrawn everyday for measuring pH. Cells were observed under an inverted phase contrast microscope to visually confirm cell growth.

Figure 4:
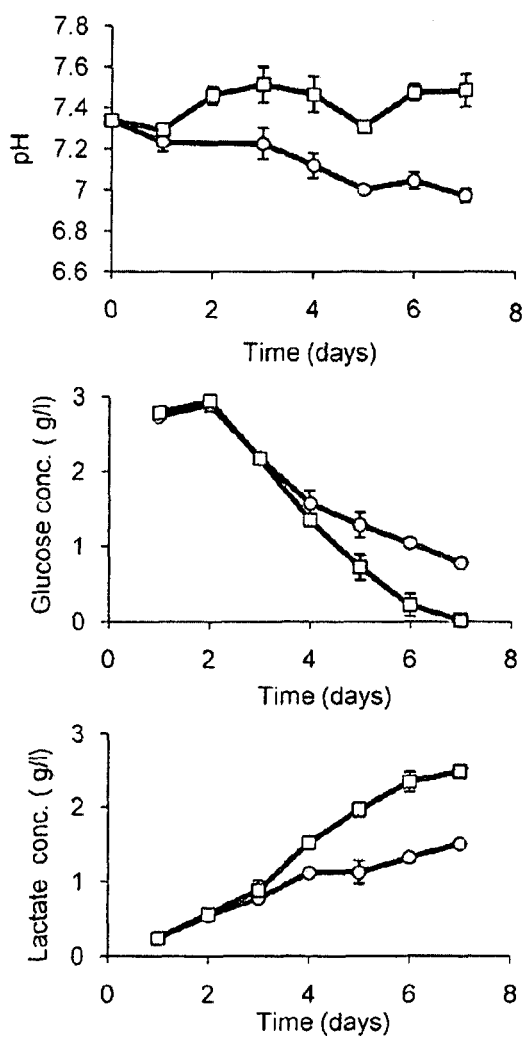
FIG. 4 depicts effect of pHmH-1 disc addition on pH of adherent A549 culture. Cells were seeded in 8 mL DMEM: F12 containing 10% FBS in 25 $cm^2$ TC flasks and incubated at 37° C., 5% $CO_2$, with two pHmH-1 discs (square) or without (circle) pHmH-1 disc. Cultures were sampled to measure pH, glucose and lactate concentrations. N=3, ±SD.

The pH in the control flasks decreased over seven days (FIG. 4), while that in the flasks with two pHmH-1 discs was maintained between 7.3 to 7.5 over seven days (FIG. 4).

Example 7

Preparation of Poly-HEMA Hydrogels Loaded with Glucose

Gels made were the polymers of 0.5%. Azobisisobutyronitrile (AIBN—as initiator) solution (w/v) in Hydroxyethylmethacrylate (HEMA) with 5% v/v Ethylene glycol dimethylacrylate (EGDMA as cross linker). Inner surfaces of glass tubes (with flat bottom) of 1.4 mm inner diameter were coated with Silanization solution (5% dichlorodimethylsilane (v/v) in heptane), to make the surface hydrophobic. These were then dried in oven for 15 minutes at 50° C. These were then filled with 625 mg glucose and 50 mg $Mg(OH)_2$. 600 µl of HEMA+EGDMA+AIBM mixture was added to 625 mg glucose+50 mg $Mg(OH)_2$ and allowed to polymerize in water bath for 1 hour at 75° C. The gels formed were then removed off the tube by breaking the tube, washed for half an hour in RO water. Before addition to media, they were surface sterilised with 70% ethanol, rinsed well in sterile water and used.

Example 8 pH Management in *E. coli* K12

To check the effect of addition of pHmH-2 in *E. coli* K12 cultures, hydrogel was added to the culture medium at indicated times. *E. coli* K12 was cultured in 20 ml Modified Willms and Reuss medium containing 200 mM MOPS and glucose as the carbon source. The modified Willms and Reuss medium was prepared as described by (Scheidle et al., 2011) consists of 20 g/L glucose; 5 g/L $(NH_4)_2SO_4$; 0.5 g/L $NH_4Cl$; 3 g/L $K_2HPO_4$; 2 g/L $Na_2SO_4$; 0.5 g/L $MgSO_4.7H_2O$; 0.01 g/L thiamine hydrochloride; 1 mL/L trace element solution (0.54 g/L $ZnSO_4.7H_2O$; 0.48 g/L $CuSO_4.5H_2O$; 0.3 g/L $MnSO_4$—$H_2O$; 0.54 g/L $CoCl_2.6H_2O$; 41.76 g/L $FeCl_3.6H_2O$; 1.98 g/L $CaCl_2.2H_2O$; 33.39 g/L $Na_2EDTA$. 3-(N-morpholino) propanesulfonic acid (MOPS) was added at indicated concentrations in some experiments.

The pHmH-2 hydrogels used in the study were autoclaved at 15 psi and 121° C. for 20 minutes before their addition in *E. coli* K12 cultures. The cultures were maintained in a shaker incubator at 37° C. with a shaking speed of 250 rpm. Hydrogel was not added to control cultures. Hydrogels were added at (a) Single pHmH-2 at beginning of culture, (b) One at the beginning and one 4 hours after inoculation and (c) Two pHmH-2 at the beginning of the culture. All the culture flasks were sampled at regular intervals for the measurement of optical density at 600 nm.

Figure 8:
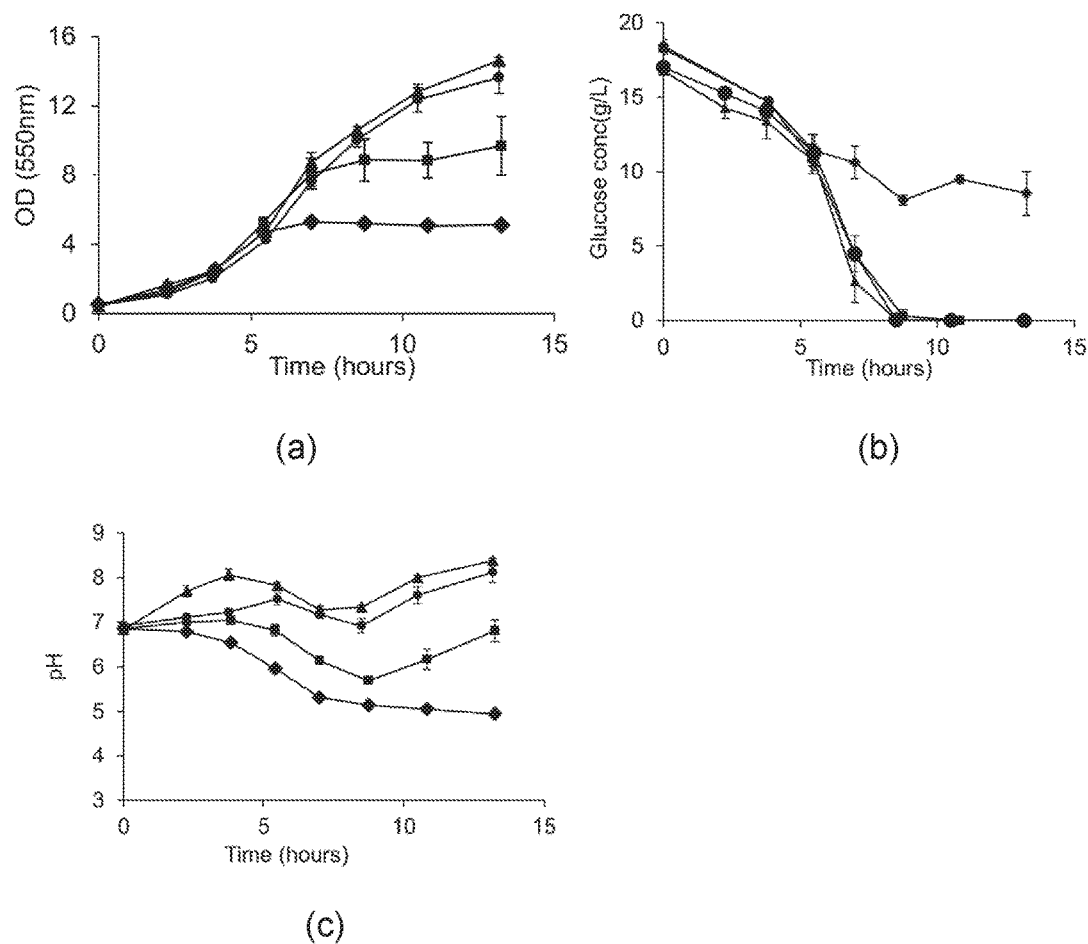
FIG. 8 depicts (a) Growth of E. coli K12 in Modified Wilms and Reuss medium with 200 mM MOPS, with and without pHmH-2 (b) Glucose consumption of E. coli K12 with and without pHmH-2 (c) pH profiles of E. coli K12 with and without pHmH-2. Control, without pHmH-2 ♦, With single pHmH-2 ■ and with staggered addition of two pHmH-2 ●, simultaneous addition of two pHmH-2 Δ.

Cultures grown in Modified Wilms and Reuss medium containing 200 mM MOPS reached an optical density of 5.2 (FIG. 8). A single pHmH-2 was added at the time of inoculation in all except the control culture. Two pHmH-2 were added at the time of inoculation to culture with simultaneous addition of two hydrogels. Staggered addition of hydrogels, one hydrogel at the time of inoculation and another at about 4 hours from time of inoculation allows the optical density to reach a maximum value of 14 with a threefold increase in final biomass yield.

Figure 7:
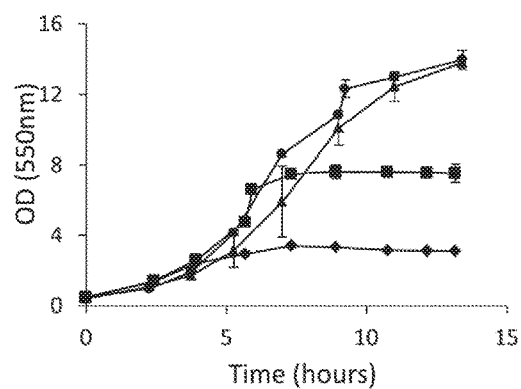
FIG. 7 depicts (a) Growth of E. coli K12 in Modified Wilms and Reuss medium with 50 mM MOPS, with and without pHmH-2 (b) Glucose consumption of E. coli K12 with and without pHmH-2 (c) pH profiles of E. coli K12 with and without pHmH-2. Control, without pHmH-2 ♦, With single pHmH-2 ■ and with staggered addition of two pHmH-2 ●, simultaneous addition of two pHmH-2 Δ.
Figure 7:
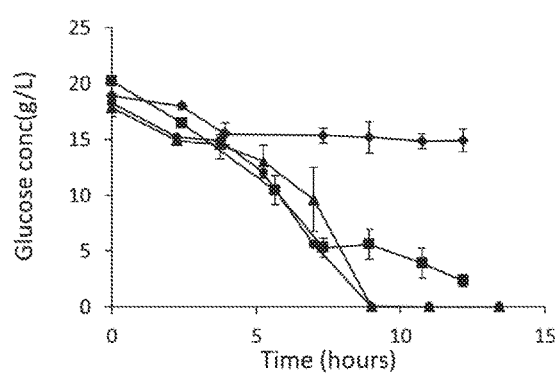
Figure 7:
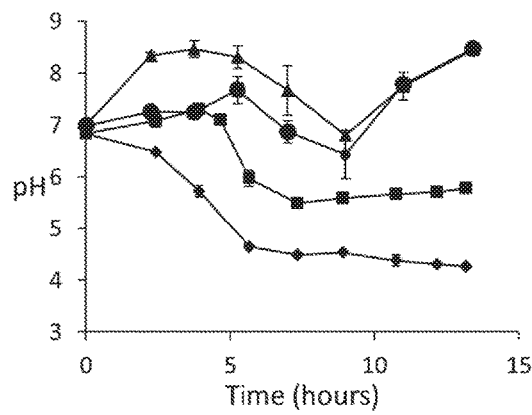

With reference to FIG. 6, the fore mentioned experiment was conducted with no MOPS, FIG. 7 is with 50 mM MOPS. It may be concluded that while the hydrogels promote better cell growth in all cases, addition of buffer further improves pH management of culture. Also, it may be concluded that staggered addition of pHmH as described herein may be resorted to for better culture performance and retains the pH management efficiency of the system.

Example 9 pH Management in *E. coli* for Plasmid Production

The effect of addition of pHmH-2 on plasmid yield in an *E. coli* strain transformed with a plasmid was investigated. Luria Bertani broth consists of 10 g/L tryptone, 5 g/L yeast extract and 10 g/L NaCl. 20 g/L glucose was added to LB broth to serve as carbon source.

Figure 9:
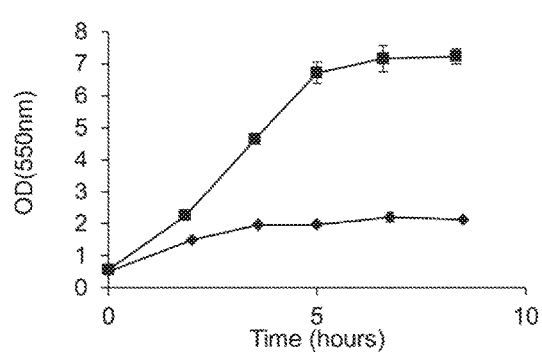
FIG. 9 depicts (a) Growth of TOP10 E. coli cells transformed with a 5 Kb plasmid, in LB-Glucose with and without pHmH-2 addition. (b) Glucose consumption (c) pH profiles. Without poly-HEMA pHmH-2 ♦, With staggered addition of two pHmH-2 ■ (d) Plasmid DNA yields from cultures with and without pHmH-2 loaded with $Mg(OH)_2$.
Figure 9:
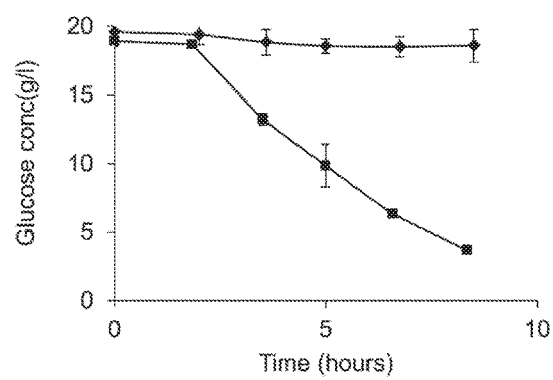
Figure 9:
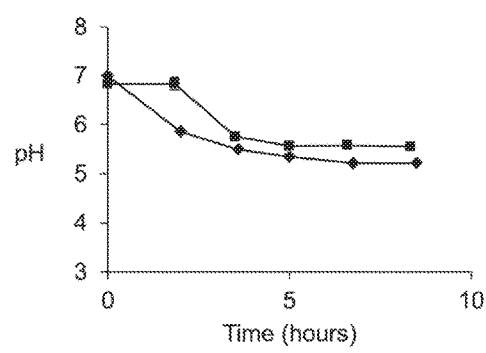
Figure 9:
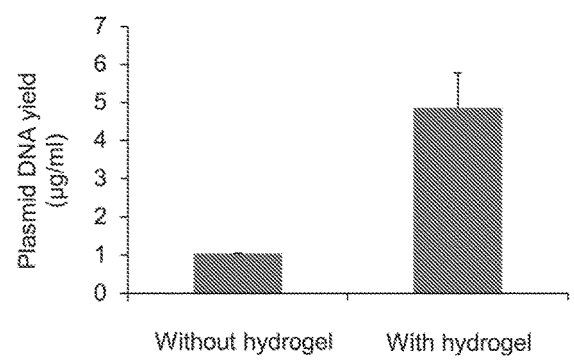

This strain was grown in 20 ml LB medium containing 20 g/l glucose and 100 µg/ml ampicillin. To compare the plasmid yield cultures of *E. coli* were grown with and without pHmH-2. One pHmH-2 was added at the beginning of the culture and another one was added 2 hours after inoculation. After 8 hours of inoculation, 1 ml of sample was taken from control flasks and from the flasks containing hydrogels. These samples were harvested by centrifugation at 10,000 rpm for 5 min, the medium was decanted and the pellet was stored at −80° C. for further processing for plasmid DNA purification. Plasmid DNA was purified using QIAprep Spin Miniprep Kit from QIAGEN, Hilden, Germany. FIG. 9 shows the plasmid yields from control cultures and pHmH-2 added cultures. The purified Plasmid DNA was quantified by measuring the absorbance at 260 nm using a NanoDrop 2000 Spectrophotometer.

With reference to FIG. 5, LB medium with 20 g/lt glucose was inoculated with *E. coli* K 12.

Example 10

Addition of pHmH-3 and Glucose Loaded Hydrogel

*E. coli* TOP 10 transformed with plasmid was cultured in LB with addition of both glucose loaded hydrogels and pHmH-3. Control cultures were cultured in LB with no hydrogels added and harvested after 14 hours.

50 ml cultures of *E. coli* TOP10 were cultured in LB supplemented with 100 µg/ml ampicillin in 250 ml shake flasks. Cultures were inoculated at an OD of 0.1 and were incubated at 250 rpm at 37° C. When the culture OD reached approximately 2, only the glucose loaded hydrogel or the glucose loaded hydrogels and pHmH-3 were added respectively. Cultures were incubated for a further 15 hours. Control cultures with no hydrogel addition were inoculated from an overnight culture in LB+ ampicillin by a 500-fold dilution and cultured further for 14 hours. 1 ml of sample was taken at harvest.

Table 1 lists the final $OD_{550}$, pH and plasmid yields in the three conditions. The cultures with both the glucose loaded hydrogels and pHmH-3 showed a 348% increase in OD and a 394% increase in plasmid yields compared to the control cultures. The pH at the end of the culture was similar to the control.

TABLE 1

Effect of hydrogel addition on volumetric plasmid yield. $OD_{550}$, final culture pH and volumetric plasmid yield in control cultures in LB, and cultures in LB with glucose loaded hydrogels with pHmH-1. 95% confidence intervals are reported.

|  | $OD_{550}$ | Final pH | Plasmid yield (µg/ml) |
| --- | --- | --- | --- |
| control | 2.5 ± 0.1 | 8.6 ± 0.1 | 7.7 ± 1.9 |
| With glucose loaded gel and pHmH-3 | 11.2 ± 0.6 | 8.2 ± 0.2 | 38.0 ± 2.4 |
| With glucose loaded hydrogel | 3.8 ± 0.2 | 5.1 ± 0.04 | 5.9 ± 0.7 |

ADVANTAGES OF INVENTION

1. In-situ management of pH
2. Enables increase in biomass and/or product
3. Applicable to adherent mammalian cells, mammalian cells in suspension, microbial cells, microbial cells expressing plasmids What claimed is:

1. A system for in situ management of pH of a culture comprising a carrier and a base, wherein said base is $Mg(OH)_2$ or $Ca(OH)_2$, and said carrier is selected from the group consisting of a hydrogel, a polymer matrix comprising a silicone elastomer, an encapsulation for said base, a membrane and a coating film, wherein release rate of said base is dependent on pH of the culture, said carrier is non-responsive to pH change of said culture, and wherein the carrier is loaded with the base.

2. The system of claim 1, wherein the carrier is a hydrogel.

3. The system of claim 2, wherein the hydrogel comprises 2-hydroxyethyl methacrylate (HEMA) as monomer; Azoisobutyronitrile, (AIBN) as initiator and optionally ethylene glycol dimethacrylate (EGDMA) as cross linker.

4. The system of claim 3, wherein an amount of the HEMA is from 71.8 to 99.9% by weight of total amount of the hydrogel.

5. The system of claim 4, wherein the base is loaded in the carrier in a manner selected from the group consisting of:
the base is dispersed in the carrier, and
the base is included in a reservoir within the carrier.

6. The system of claim 1, wherein said culture comprises medium and cells selected from the group consisting of unmodified animal cells, genetically modified animal cells, microbial cells, insect cells, stem cells and mesenchymal stem cells.

7. The system of claim 1, wherein said culture is grown in a medium comprising glucose, and optionally a buffer.

8. The system of claim 1, wherein the pH of the culture is managed between 5-9.

9. The system of claim 1, wherein the pH of the culture is managed for a period of up to 15 days.

10. The system of claim 1, wherein $Mg(OH)_2$ or $Ca(OH)_2$ is released depending on pH of the culture.

11. The system of claim 1, wherein $Mg(OH)_2$ or $Ca(OH)_2$ is released depending on pH of the culture, and wherein said pH dependent-release of $Mg(OH)_2$ or $Ca(OH)_2$ is independent of the carrier.

12. The system of claim 1, wherein the in situ management does not require periodic measurement of pH.

13. The system of claim 1, wherein the system comprises two discs of the carrier.

14. A process for in situ management of pH of a culture, the process comprising employing a system comprising;
a carrier selected from the group consisting of a hydrogel, a polymer matrix comprising a silicone elastomer, an encapsulation for said base, a membrane and a coating film, wherein said carrier is non-responsive to pH change of said culture; and
a base, wherein said base is $Mg(OH)_2$ or $Ca(OH)_2$, wherein release rate of said base is dependent on pH of the culture, and the carrier is loaded with the base.

* * * * *